United States Patent [19]

Goni et al.

[11] Patent Number: 4,956,362
[45] Date of Patent: Sep. 11, 1990

[54] USE OF CARPIPRAMINE FOR THE TREATMENT OF ANXIETY AND SLEEP DISORDERS

[75] Inventors: Sylvie Goni, Paris; Odile Piot, Choisy le Roi; Jean-Luc Zundel, Paris, all of France

[73] Assignee: Rhone-Poulenc Sante, a French Body Corporate, France

[21] Appl. No.: 450,084

[22] Filed: Dec. 13, 1989

[30] Foreign Application Priority Data

Dec. 16, 1988 [FR] France ............................. 88 16606

[51] Int. Cl.$^5$ ............................................. A61K 31/54
[52] U.S. Cl. ...................................................... 514/217
[58] Field of Search ............................................. 514/224

[56] References Cited

PUBLICATIONS

Arzneimittel-Forschung, vol. 7, No. 18, Juillet 1968, pp. 1435-1441.

*Primary Examiner*—Stanley J. Friedman
*Attorney, Agent, or Firm*—Stevens, Davis, Miller & Mosher

[57] ABSTRACT

Carpipramine, and its pharmaceutically acceptable salts, are useful for the treatment of anxiety and sleep disorder.

2 Claims, No Drawings

USE OF CARPIPRAMINE FOR THE TREATMENT OF ANXIETY AND SLEEP DISORDERS

The present invention relates to the use of carpipramine, or a pharmaceutically acceptable salt of this compound.

Carpipramine, or 5-[3-(4-carbamoyl-4-piperidinopiperidino)-1-propyl]-10,11-dihydrodibenz[b,f]azepine, described for example in BSM (French Medicament Patent) No. 3872M, is useful in the treatment of psychoses, and in particular of schizophrenia.

It has now been found that carpipramine, and its pharmaceutically acceptable salts, possesses antagonist properties with respect to serotonin (5-HT$_2$ receptors), and is useful in the treatment of anxiety and sleep disorders.

The affinity of carpipramine for central serotonin receptor sites (type S$_2$) was determined by a technique based on that of J. E. LEYSEN et al., Mol. Pharmacol. 21, 301 (1982), which consists in measuring the affinity of the product for binding sites for tritiated ketanserin. In this test, the IC$_{50}$ of carpipramine is 3 nM.

Carpipramine has also been found to be an antagonist of mescaline-induced heat twitches in mice, using a technique based on that of S. J. CORNE and R. W. PICKERING, Psychopharmacologia, 11, 65–78 (1967). In this test, the AD$_{50}$ of subcutaneously administered carpipramine is 8 mg/kg.

Carpipramine displays low toxicity. Its LD$_{50}$ is equal to 250 mg/kg when administered orally in mice.

The invention accordingly provides medicaments for the treatment of anxiety or a sleep disorder comprising carpipramine or a pharmaceutically acceptable salt thereof, and a method of treating anxiety or a sleep disorder which comprises administering to a subject in need of such treatment an effective amount of carpipramine or a pharmaceutically acceptable salt thereof.

Carpipramine and its pharmaceutically acceptable salts may be prepared by the process described in the aforesaid BSM No. 3872 M.

As examples of pharmaceutically acceptable salts, the addition salts with inorganic acids, such as the hydrochloride, sulphate, nitrate and phosphate, or organic acids, such as the acetate, propionate, oxalate, succinate, benzoate, fumarate, maleate, methanesulphonate, isethionate, theophylline acetate, salicylate, phenolphthalinate and methylenebis($\beta$-hydroxynaphthoate), or substitution derivatives of these compounds, may be mentioned.

Carpipramine may be used for the treatment of anxiety and sleep disorders in the form of a medicament consisting of carpipramine, or a pharmaceutically acceptable salt thereof, in the pure state or in the form of a composition in which it is combined with another pharmaceutically compatible product, which can be inert or physiologically active. Such medicaments can, in particular, be used orally, parenterally or rectally.

Solid compositions for oral administration may be, for example, tablets, pills, powders (gelatin capsules, wafer capsules) or granules. In these compositions, the active principle is mixed with one or more inert diluents such as starch, cellulose, sucrose, lactose or silica. These compositions can also comprise substances other than diluents, e.g. one or more lubricants such as magnesium stearate or talc, a colouring, a coating (dragee) or a varnish.

Liquid compositions for oral administration include solutions, suspensions, emulsions, syrups and elixirs of a pharmaceutically acceptable nature, containing inert diluents such as water, ethanol, glycerol, vegetable oils or liquid paraffin. These compositions, e.g. wetting agents, sweeteners, thickeners, flavourings or stabilizers.

Sterile compositions for parenteral administration are preferably suspensions, emulsions or non-aqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, for example by aseptic filtration, by incorporating sterilizing agents in the composition, by irradiation or by heating. They may also be prepared in the form of sterile solid compositions which can be dissolved at the time of use in sterile water or any other sterile injectable medium.

Compositions for rectal administration are suppositories or rectal capsules which contain, apart from the active product, excipients such as cocoa butter, semi-synthetic glycerides or polyethylene glycols.

Carpipramine, and its pharmaceutically acceptable salts, are useful in human therapy in the treatment of anxiety and sleep disorders. The dose used depends on the effect sought, the treatment period and the administration route used. It is generally between 10 and 400 mg per day orally for an adult, with unit doses ranging from 2 to 50 mg of active substance.

Generally speaking, the doctor will determine the appropriate dosage in accordance with the age and weight and all other factors specific to the subject to be treated.

The examples which follow illustrate pharmaceutical compositions.

EXAMPLE A

Hard gelatin capsules containing 25 mg of active product and having the following composition are prepared by the usual technique:
carpipramine: 25 mg
microcrystalline cellulose: 75 mg
mannitol: 41 mg
colloidal silica: 4 mg
carboxymethylstarch sodium: 25 mg
talc: 18 mg
magnesium stearate: 2 mg
polyvidone excipient: 10 mg

EXAMPLE B

Tablets containing 50 mg of active product and having the following composition are prepared by the usual technique:
carpipramine dihydrochloride: 50 mg
monocrystalline cellulose: 75 mg
mannitol: 41 mg
polyvidone excipient: 10 mg
carboxymethylstarch: 25 mg
colloidal silica: 4 mg
talc: 18 mg
magnesium stearate: 2 mg
mixture of hydroxymethyl cellulose, glycerol and titanium oxide (72:3.5:24.5): 11 finished
film-coated tablet weighing: 245 mg

EXAMPLE C

An injectable solution containing 10 mg of active product and having the following composition is prepared:

carpipramine: 10 mg
benzoic acid: 80 mg
benzyl alcohol: 0.06 cc
sodium benzoate: 80 mg
ethanol, 95%: 0.4 cc
sodium hydroxide: 24 mg
propylene glycol: 1.6 cc
water q.s.: 4 cc

We claim:

1. Method of treating anxiety or a sleep disorder which comprises administering to a subject in need of such treatment an effective amount of carpipramine or a pharmaceutically acceptable salt thereof.

2. Method according to claim 1 in which the amount administered is 10 to 400 mg per day orally.

* * * * *